Figure 2:
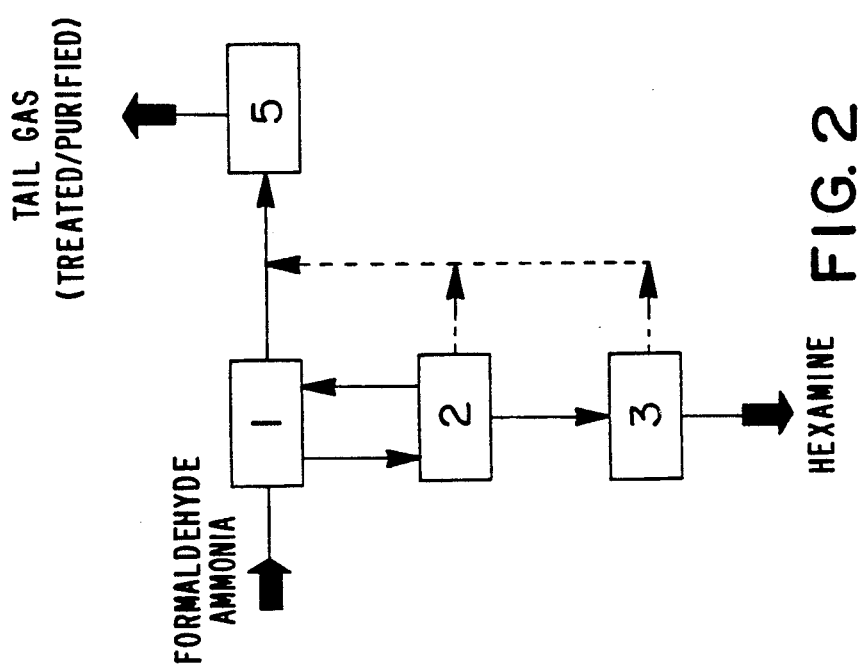

United States Patent [19]

Hermann et al.

[11] Patent Number: 5,187,274
[45] Date of Patent: Feb. 16, 1993

[54] PROCESS TO AVOID THE FORMATION OF WASTE WATER DURING HEXAMINE PRODUCTION

[75] Inventors: Heinrich Hermann, Cologne; Gunther Pelster, Sankt-Augustin; Klaus Degener, Cologne, all of Fed. Rep. of Germany

[73] Assignee: Josef Meissner GmbH & Co., Cologne, Fed. Rep. of Germany

[21] Appl. No.: 732,971

[22] Filed: Jul. 19, 1991

[30] Foreign Application Priority Data

Jul. 24, 1990 [DE] Fed. Rep. of Germany ....... 4023476

[51] Int. Cl.⁵ .................................. C07D 487/12
[52] U.S. Cl. .................... 544/186; 544/179
[58] Field of Search ..................... 544/179, 186

[56] References Cited

U.S. PATENT DOCUMENTS 3,538,199  11/1970  Weiss et al. ................. 544/186

FOREIGN PATENT DOCUMENTS 0510326  2/1955  Canada .................. 544/186

OTHER PUBLICATIONS

Meissner et al., "Industrial and Engineering Chemistry", vol. 46(4), pp. 724–727, 1954.

Primary Examiner—Nicholas S. Rizzo
Assistant Examiner—Y. N. Gupta
Attorney, Agent, or Firm—Sprung Horn Kramer & Woods

[57] ABSTRACT

In a process to avoid the formation of waste water in the production of hexamine from ammonia and the stream of gas containing formaldehyde resulting from the catalytic oxidation of methanol on metallic oxide catalysts, or by oxidative dehydrogenation to formaldehyde, the liquid volume during reaction for the production of hexamine is kept constant, and carbon monoxide, the organic components of the exhaust gas and also hydrogen, if present, are oxidized to carbon dioxide and water, thus avoiding an energy-consuming condensation of the condensable components from the stream of exhaust gas and their treatment.

9 Claims, 1 Drawing Sheet

PROCESS TO AVOID THE FORMATION OF WASTE WATER DURING HEXAMINE PRODUCTION

DESCRIPTION

Hexamethylene tetramine (1,3,5,7-tetraazaadamanthane), briefly called hexamine, is produced by reaction of formaldehyde with ammonia according to the following reaction equation:

$$6\ CH_2O + 4\ NH_3 \rightarrow (CH_2)_6N_4 + 6\ H_2O.$$

According to the known processes, the reactants are contacted as gas or aqueous solution in aqueous phase in such a way that a neutral solution of hexamethylene tetramine in water is obtained.

The excess water is distilled off from the thus produced aqueous solutions and the formed hexamine crystals are separated by filtration, thoroughly rinsed using water or other solvents and dried. The mother-lyes after filtration are recycled as reaction solution into the process.

The embodiment preferred nowadays for the production of hexamine is the direct reaction of formaldehyde-process-gas from oxidative dehydrogenation or oxidation of methanol with ammonia in an aqueous solution.

In the case of oxidation of methanol, for example on metallic oxide catalysts, the methanol is converted into formaldehyde, whereby—besides unconverted methanol—a number of undesired by-products, as carbon monoxide, dimethylether and dimethoxymethane, are formed that are dragged along as contaminations through the subsequent hexamine production.

The formaldehyde-process-gas from oxidative dehydrogenation of methanol, for example, according to the silver contact process, contains—in addition to unconverted methanol—as by-products hydrogen, carbon monoxide, methane, methyl formate, formic acid and carbon dioxide.

For further details about the technical production of formaldehyde, among others by oxidation of hydrocarbons, reference is made to Winnacker/Küchler, Chemische Technologie, 4th edition, vol. No. 6 (Organische Technologie II), pages 62 to 66.

For the continuous production of hexamine the formaldehyde-process-gas is converted at a temperature from 70° to 200° C.—preferably from 120° to 150° C.—with gaseous ammonia at an absolute pressure from 500 mbar to 1.5 bar—preferably from 1013 mbar to 1.2 bar—in an appropriate reactor. The liquid phase—together with the crystallized hexamine—is continuously discharged from the reactor. The hexamine crystals are separated, washed, and the mother-lye is again recycled into the reaction. The wet hexamine crystals are dried, and, if necessary, mixed with an anti-caking agent and packed.

The inert gases introduced into the reactor as components of the process gas, the produced or excess water and the by-products originating from the formaldehyde-process-gas are removed from the hexamine reactor at a certain temperature of the reaction solution (AT-PS 178 889; FR-PS 1 080 353). This gas stream containing about 75 to 80 mole % of inert gas, water and less than 0.5 mole % of methanol and the various by-products from the formaldehyde production is—together with the exhaust air from filtration and drying of the hexamine—by cooling and separation freed from its condensable components as water, methanol, formaldehyde and ammonia. A condensate containing 0.5 to 3.5% of methanol and traces of formaldehyde, ammonia, dimethylether, formic acid and hexamine is obtained from which, before discharge into an outfall ditch, the methanol and other traces—above all, ammonia and formaldehyde—must be removed. After condensation the exhaust gas stream is either discharged directly to atmosphere or after a further treatment step, e.g., an exhaust gas combustion, where it is freed from uncondensable components as carbon monoxide, hydrogen, dimethylether, and also from traces of methanol, formaldehyde or ammonia.

Therefore, the object of the invention is to provide a process for the production of hexamine where no waste water occurs that still has to be treated and purified because of the high methanol content from 0.5 to 10% and the other dissolved organic contaminations and ammonia before being discharged.

This necessary treatment—in order to be able to attain the limit values stipulated by law concerning the introduction into an outfall ditch—is complex and expensive.

In order to achieve the object of the invention—namely to avoid the formation of waste water having to be treated during the production of hexamine from formaldehyde and ammonia—the contaminations dragged along from the preceding process steps, the unconverted starting compounds and the excess of water from the reaction of formaldehyde with ammonia after leaving the hexamine rector are no longer divided into two mass streams that are treated so as to be able to discharge them as exhaust gas or waste water into the environment. Instead, the entire stream of exhaust gas, i.e., condensable and uncondensable matter from the reaction of formaldehyde and ammonia, is removed directly from the hexamine reactor and—together with the exhaust air from separation and drying of the hexamine—subjected to an oxidative treatment, permitting to free the stream of exhaust gas completely from condensable and uncondensable organic and inorganic contaminations and then to discharge it as gas into the environment.

A catalytic combustion as well as a thermal treatment come into consideration for the oxidative treatment of the exhaust gases. The thereby available thermal energy can be used in the process, e.g., for drying the separated hexamine or preheating the foreign gases additionally introduced into the process.

Oxidation of the exhaust gas components allows to dispense with the hitherto necessary condensation, recovery of methanol and waste water treatment. Thus the increasingly more severe requirements in respect of environmental compatibility and elimination of pollutants are fulfilled. The consumption of cooling water and electrical energy is considerably reduced by the process according to the invention.

The temperature of the reaction of formaldehyde and ammonia in the hexamine reactor is preferably controlled so that methanol, water and reaction water are completely removed from the reactor with the stream of exhaust gas and thus the liquid volume in the reactor is kept constant.

Moreover, the reaction temperature is selected so that the temperature of the reaction gas leaving the hexamine reactor does not drop below the dew point. In this way it is ensured that the gas phase does not become saturated with the condensables and that their condensation does not occur.

Operations are preferably carried out within a temperature range from 50° to 75° C., and especially in that from 60° to 70° C.

Inert foreign gas can be introduced additionally into the reaction mixture, entailing the advantage that the considerable amounts of water being present in the form of reaction water or as a component of the process gas in the case of he metallic oxide process as well as in the case of the silver contact process can be safely removed by the addition of foreign gas so that the liquid volume in the reactor is kept constant. Advantageously, the tail gas from the oxidative reaction of the exhaust gases from the reaction to produce hexamine, or foreign gas heated by this oxidative reaction, can be used as inert foreign gases. The additional use of an inert foreign gas is even advantageous if the temperature during the reaction of formaldehyde and ammonia is comparatively low, i.e., if it does not rise above 60° C.

Under these conditions also a reaction under reduced pressure can be carried out advantageously. This could be an advantage if the reaction temperature in the hexamine reactor is below the boiling point of the reaction mixture and it becomes difficult for that reason to evaporate sufficient water.

As far as the gas stream containing formaldehyde is obtained by reaction on metallic oxide catalysts, the exhaust gas of the hexamine formation is preferably oxidized catalytically, whereas it is preferably burnt if the gas stream containing formaldehyde originates from the silver contact process. The energy obtained by means of this process step may be used for drying the filtered and recrystallized hexamine. According to the hitherto known processes the reaction energy resulting from the production of hexamine suffices to keep the reaction mixture at a temperature around the boiling point of the reaction mixture, but it is not sufficient for drying the washed hexamine crystals.

Figure 1:
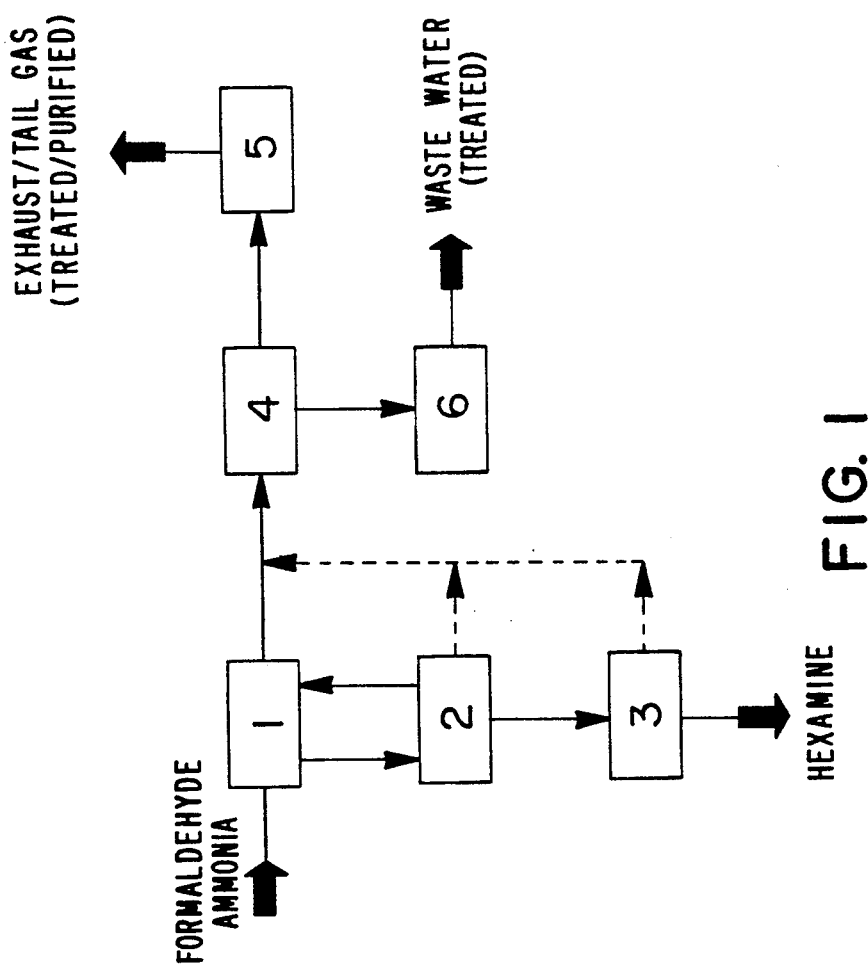

The invention will be further described with reference to the accompanying drawing wherein:

FIG. 1 is a flow sheet of the known process for continuously producing hexamine and treating the product; and FIG. 2 is a flow sheet of the novel process.

Referring now more particularly to the drawing, in FIG. 1 there is shown a reactor 1 to which the reactants are supplied. The hexamine crystals are separated in vessel 2 and passed to dryer 3. The liquid from 2 is recycled to reactor 1.

Exhaust gases from 2 to 3 are added to the gas stream leaving reactor 1 and together pass to condenser 4. Liquid run off from condenser 4 passes to vessel 6 and gas from 4 passes to treater 5.

In the novel system of FIG. 2, gases from 1, 2 and 3 are directly oxidized in 5, eliminating condenser 4 and vessel 6.

The invention is further illustrated in the following two embodiments.

I. A stream of process gas from a metallic oxide process, having the composition indicated in column 1 of Table 1, is cooled to about 110° C. and introduced into the hexamine reactor. Simultaneously, ammonia is fed. The temperature of the reaction to hexamine—while using the heat thereby released—is kept constant at about 65° C.

At this temperature the condensable components are completely kept in the gas phase or transferred into it. The stream of exhaust gas, free from formaldehyde, with a composition according to Table 1, column 2, is fed to the oxidation.

TABLE 1

| | Composition of process gas from the metallic oxide process before feeding to and after leaving the hexamine reactor. | |
|---|---|---|
| Gas | before hexamine reactor mole % | after hexamine reactor mole % |
| $N_2$ | 70.69 | 63.70 |
| $O_2$ | 15.41 | 13.89 |
| $H_2O$ | 7.67 | 21.98 |
| $CH_2O$ | 5.77 | 0.01 |
| $CH_3OH$ | 0.12 | 0.10 |
| CO | 0.31 | 0.28 |
| $C_2H_6O$ | 0.03 | 0.03 |
| | 100.00 mole % | 100.00 mole % |

The crystalline hexamine is separated from the mother-lye in the filtration step arranged behind the hexamine reactor and subsequently washed. The mother-lye and wash water from product washing are then recycled into the hexamine reactor. The hexamine crystals are dried after washing. The streams of gas originating from washing and drying are likewise transferred to exhaust gas oxidation.

By means of the heat produced thereby catalytic oxidation the hexamine crystals are dried.

II. A stream of process gas containing formaldehyde is obtained by way of an oxidative dehydrogenation in the case of the silver contact process and has the composition shown in Table 2, column 1.

This process gas is introduced into the hexamine reactor at a temperature of about 110° C. and converted there with ammonia at a temperature of 70° C.

The exhaust gas leaving the hexamine reactor has the composition shown in Table 2, column 2.

TABLE 2

| | Composition of process gas from the silver contact process before feeding and after leaving the hexamine reactor. | |
|---|---|---|
| Gas | before hexamine reactor mole % | after hexamine reactor mole % |
| $N_2$ | 35.14 | 34.87 |
| $O_2$ | 0.12 | 0.13 |
| $H_2O$ | 37.92 | 55.52 |
| $CH_2O$ | 17.44 | 0.01 |
| $CH_3OH$ | 1.76 | 2.10 |
| CO | 1.85 | 1.84 |
| $H_2$ | 5.77 | 5.54 |
| | 100.00 mole % | 100.00 mole % |

In order to avoid condensation at these reaction temperatures as much inert gas, e.g. nitrogen, may be added to this mixture as is needed to keep the temperature of the exhaust gas from the hexamine reactor above the dew point.

This hydrogen-containing exhaust gas, too, is fed to a combustion. The energy produced by this combustion is used for drying the product or preheating the added stream of foreign gas.

It will be understood that the specification and examples are illustrative but not limitative of the present invention and that other embodiments within the spirit and scope of the invention will suggest themselves to those skilled in the art.

We claim:

1. In the process comprising oxidatively dehydrogenating or oxidizing methanol to form a gas stream containing formaldehyde and reacting said gas-stream with ammonia in aqueous phase, thereby forming hexamine crystals and a gaseous waste stream of unreacted formaldehyde and waste water, the improvement which comprises maintaining the liquid volume of the aqueous phase constant during the reaction, and oxidizing the waste gas stream to convert organic components by discharging any introduced methanol and water and also the reaction water from the hexamine reactor together with the stream of exhaust gas, carbon monoxide and any hydrogen contained therein to carbon dioxide and water.

2. A process according to claim 1, wherein the temperature of the exhaust gas is kept above the dew point.

3. A process according to claim 1, including the additional step of introducing into the reaction mixture a foreign gas which is inert to the reaction.

4. A process according to claim 3, wherein the foreign gas is the tail gas of the oxidative reaction of the exhaust gases from the reaction of the hexamine production.

5. A process according to claim 4, wherein the foreign gas is heated by said oxidative reaction.

6. A process according to claim 1, wherein the reaction is carried out under reduced pressure.

7. A process according to claim 1, wherein the reaction is carried out within the temperature range from 50° to 75° C.

8. A process according to claim 1, wherein the initial gas stream containing formaldehyde is obtained by catalytic oxidation of methanol and the exhaust gases of the reaction are oxidized catalytically.

9. A process according to claim 1, wherein the initial gas stream containing formaldehyde is obtained by oxidative dehydrogenation of methanol and the exhaust gases of the reaction are burnt.

* * * * *